United States Patent [19]

Jansheski

[11] Patent Number: 4,643,676
[45] Date of Patent: Feb. 17, 1987

[54] DENTAL TOOL FOR PERSONAL ORAL HYGIENE

[75] Inventor: John E. Jansheski, Tiburon, Calif.

[73] Assignee: U.S. DenTek Corporation, Mill Valley, Calif.

[21] Appl. No.: 833,855

[22] Filed: Feb. 26, 1986

Related U.S. Application Data

[63] Continuation-in-part of Ser. No. 747,989, Jun. 24, 1985, abandoned, which is a continuation-in-part of Ser. No. 612,738, May 21, 1984, abandoned.

[51] Int. Cl.$^4$ ............................................. A61C 15/00
[52] U.S. Cl. ................................................... 433/143
[58] Field of Search ........................ 132/90, 76.2, 89; 433/147, 141, 143

[56] References Cited

U.S. PATENT DOCUMENTS

| | | | |
|---|---|---|---|
| 1,397,395 | 11/1921 | Bixler | 433/143 |
| 1,723,226 | 8/1929 | Withycombe | 433/147 |
| 1,784,986 | 12/1930 | Eisenberg | 15/89 |
| 3,430,345 | 3/1969 | Abreu | 433/147 |
| 4,326,548 | 4/1982 | Wagner | 433/147 |

FOREIGN PATENT DOCUMENTS 2842405  4/1980  Fed. Rep. of Germany ...... 433/143

OTHER PUBLICATIONS

"Stimudent" advertisement by Johnson & Johnson in Newsweek Magazine, 4/12/1984.

Primary Examiner—Robert Peshock
Attorney, Agent, or Firm—Limbach, Limbach & Sutton

[57] ABSTRACT

A tool is described for the removal of hardened plaque and tarter from the interproximal spaces of the mouth. The tool is designed to permit self-application. The tool comprises a conically-based stainless steel pick which tapers upward to a J-shaped, curved substantially flat tip, a blunted end for said tip and an elongated substantially cylindrical handle.

1 Claim, 6 Drawing Figures

U.S. Patent  Feb. 17, 1987  4,643,676
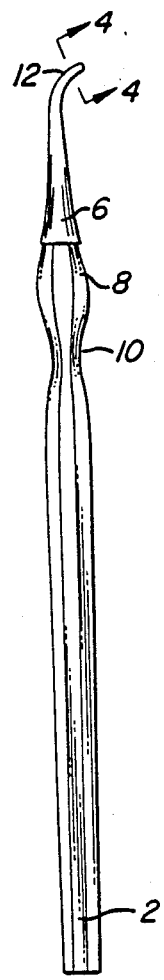
FIG._1.
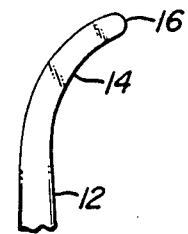
FIG._2.
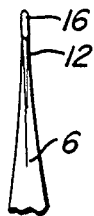
FIG._3.
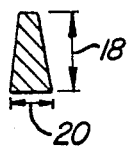
FIG._4.
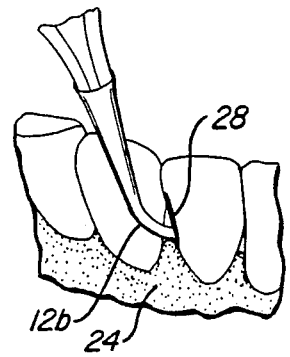
FIG._6.
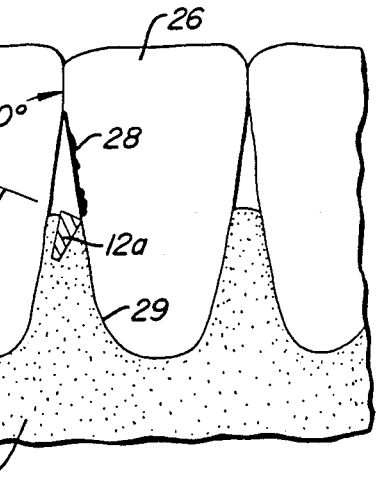
FIG._5.

DENTAL TOOL FOR PERSONAL ORAL HYGIENE

This is a continuation in part of my prior application Ser. No. 747,989, filed June 24, 1985, and now abandoned, which was a continuation in part of my prior application Ser. No. 06/612,738, filed May 21, 1984, and now abandoned.

DESCRIPTION

1. Technical Field

This invention relates to a tool for personal use in oral hygiene allowing the user to remove hardened plaque and tartar accumulations from the interproximal spaces of the mouth.

2. Background Art

Many inventions are directed to instruments for use in scaling and cleaning teeth. Commonly, this operation is performed by a dentist or hygienist; therefore, most of these instruments, are designed with the extreme environment of professional use in mind. Such conditions require the instruments to be entirely constructed of resilient materials capable of withstanding the high temperatures of sterilization. The rigors of high frequency use further determine the geometrical configuration of such instruments, often resulting in fairly thick devices incapable of penetrating the interproximal spaces of the mouth. Further the geometric design optimum for professional use differs from self-application. The angle of application which may facilitate the hygienist's use may make self scaling difficult.

One tool designed for self-applied oral hygiene is disclosed in U.S. Pat. No. 4,326,548 (Wagner) filed on June 9, 1980. In Wagner, a hooklike metal tool is described. This tool employs a probe of circular cross-section to dislodge food debris and tightly wedged particles from between the teeth. The pick holder is shaped to simulate a pen barrel with a removable cap. The working surface of this device comprises the free end terminus of the pick.

The invention herein disclosed is a self-applied tool for removing hardened plaque from the interproximal spaces of the mouth. The design angle of application and substantially flat tip of the pick permit the user to penetrate the crevices and spaces previously unreachable. The edge formed at the top of the curved segment is used to scale the hardened plaque from the teeth.

It is an object of this invention to provide an improved tool for personal oral hygiene which can be self-applied to remove hardened plaque, which is light weight and inexpensive and which is configured for convenient self-application and manipulation.

DISCLOSURE OF THE INVENTION

The tool in accordance with this invention includes a handle joined to a stainless steel pick. The pick tapers from a conical base into a hooked tip of triangular cross-section which appears substantially flat. The terminus of the hooked tip is rounded to prevent unnecessary injury to the buccal tissue of the user.

The handle contains an indentation near the top end which directs the user to grasp the tool in this location and permits the application of sufficient force to scale the teeth. The indentation identifies for the user the optimum place to grasp the instrument to maximize its utility in accordance with the angular design of the instrument. Further, this indentation represents the optimum location for digital manipulation by the user. Grasping the handle at the indentation enhances leverage and enables accurate manipulation of the tool. One end of the handle, closest the indentation, contains a cylindrical cavity into which fits the bottom of the pick.

The tool of this invention permits the user to scale hardened plaque and tartar from between the teeth. This is accomplished by grasping the handle and positioning the substantially flat tip between the teeth at an angle of approximately sixty degrees from the vertical plane of the tooth. Next the user, using light to medium pressure moves the tip up, away from the gum repeating often, thereby removing the hardened plaque and tartar. This step is repeated until the interproximal surface is clean and glasslike. The user then positions the tip in the next interproximal space, repeating until all the teeth, upper and lower, have been scaled.

BRIEF DESCRIPTION OF THE DRAWINGS

FIG. 1 is a side view of the dental tool for personal oral hygiene constructed in accordance with this invention showing the indentation in the plastic handle and the curvature of the tip.

FIG. 2 is a detailed view of the stainless steel pick as seen in FIG. 1.

FIG. 3 is a front view of the stainless steel pick.

FIG. 4 is a vertical, sectional view taken generally along the lines in FIG. 1, 4—4'.

FIG. 5 is a front view showing the tool's orientation in an interproximal space.

FIG. 6 is a side view showing the instrument and its use in the scaling step.

BEST MODE FOR CARRYING OUT THE INVENTION

This invention is directed towards an improved tool for personal oral hygiene and a method for its use. The tool enables the user to remove hardened plaque and tartar accumulations from the interproximal spaces of the mouth. The instrument and the method will be described in detail by reference to the drawings.

In the Figures it is seen that the tool consists of a steel pick 6 as mounted on a handle 2. The handle 2 is meant to be grasped by the user at the indentation 10 just below the top of the handle 8. The handle is relatively thin, quite like a pencil, facilitating the use and manipulation of this instrument. The steel pick 6 is seated on the top of the handle 8. The steel pick 6 has a conical base which tapers up to a hooked tip 12, having a generally triangular cross-section which appears substantially flat. The altitude of the conical base is selected to minimize the magnitude of leverage obtainable with the pick 6.

In FIGS. 2 and 3 details of the hooked tip are shown. This tip-end of the steel pick 6 has a generally triangular cross-section as seen in FIG. 4. This is taken along the lines 4—4' in FIG. 1. The width of the blade section of the hooked tip is determined by the altitude 18 of the triangular cross-section. In one embodiment of the invention, the altitude 18 is 39 mils. The gauge, or thickness, of the substantially flat part of the hooked tip is determined by the base 20 of the triangular cross-section. In one embodiment of the invention this measurement is 15 mils.

The radius of curvature of the hooked tip is an important feature of this instrument. For example, as this tool is self-applied, the curvature must account for access to both the upper and lower teeth in the front and back of the mouth. Other design parameters need be considered. As noted, the curved edge 14 represents the actual working surface, or edge, of this tool. This edge must be alignable with the interproximal surfaces of all of the teeth, upper and lower. Another design parameter pertinent to the degree of curvature derives from the intended self-application of this device. Whereas the majority of dental tools and instruments are designed for application by the professional, this pick 12 is designed to be self-applied. This requires consideration of a different matrix of force vectors. When externally applied, one set of force vectors is in place. The configuration of a tool is designed to maximize the relationship between the direction of applied force and the receiving surfaces. Self-application brings into play a different set of force vectors. A tool useful for self-application must account for this change in geometry and be designed for optimal utilization of these different force vectors. Since the working edge 14 is the point of application of force, its radius of curvature is vital to the proper functioning of the tool. Another design parameter for the tip is user safety. Unsupervised use of dental tools may lead to intrusions into the interproximal spaces, potentially exposing the user to painful injury to the buccal tissue. The radius of curvature of the tip 14 is partially determinative of the tool's sharpness. Irregular shapes for this probe present increased risk of injury to the user. A simple rounded tip enhances user safety. To address all of these design parameters, in one embodiment of the invention the radius of curvature 14 is selected as 0.25 inches. To further enhance user safety, the hooked tip also terminates in a blunted-end tip 16 of radius of curvature 0.019 inches to prevent injury to the buccal tissue. The stainless steel chosen for the tip 14 edges must be softer than tooth enamel to prevent damage to the surface. Stainless steel 440A may be used to contruct the tip 14.

The scaling method used in connection with the instrument of this invention is illustrated in FIGS. 5 and 6. The hooked tip 12a is inserted between the teeth 26 where hardened plaque and tartar 28 have built up on the interproximal surface of the tooth 29. The tip 12 is positioned as close to the buccal tissue 24 as possible to remove the maximum amount of plaque. The method in accordance with this invention involves the positioning of the hooked tip at approximately a 60° angle subtended by the plane of the base of the triangular cross-section 22 and the plane of the interproximal tooth surface 29. The user then moves the instrument upward scraping the hardened plaque 28 from the tooth surface 29 but due to the relative hardness of the pick edges, the tooth enamel is undamaged. This is repeated until the surface 29 of the tooth is smooth and glasslike. The user then next inserts the instrument into the succeeding interproximal space. This procedure is repeated until all of the spaces in the mouth have been scraped by said instrument. The procedure illustrated in FIG. 6 should be repeated from both the inside and the outside of the teeth 26, both upper and lower teeth.

Although the foregoing invention has been described in some detail by way of illustration and example for purposes of clarity, it will be obvious to those skilled in the art that certain changes and modifications may be practiced within the scope of the appended claims.

I claim:

1. A dental tool for self-application to the interproximal spaces of the mouth to remove food accumulations, hardened plaque and tartar which comprises:
   (a) a conically-based stainless steel pick which tapers upward to a J-shaped, curved substantially flat tip and which forms two edges on the inside of said J-shaped tip useful for scraping tartar from tooth enamel surfaces, said tip, constructed from stainless steel softer than said tooth enamel surfaces, having a radius of curvature selected to compliment self-application towards interproximal spaces of the mouth and a small gauge to permit insertion into said interproximal spaces and the altitude of such conical base selected to minimize the magnitude of leverage obtainable with said pick;
   (b) a blunted end for said tip to prevent damage to buccal tissues of the applicant; and,
   (c) an elongated, substantially cylindrical handle, which at one end is fastened to and is subtended from said conically based pick, said handle containing an indentation at the end closest the pick which indentation is positioned completely and radially about the longitudinal axis of the handle to permit more accurate and effective manipulation of the pick in the mouth and to identify to the user the optimum location to grasp the handle.

* * * * *